United States Patent [19]  
Denzel et al.

[11] 4,000,277  
[45] Dec. 28, 1976

[54] 3,11-DIHYDRO-6H-PYRAZOLO[1,5-a]PYRAZOLO[4',3':5,6]PYRIDO[4,3-d]PYRIMIDIN-6-ONE AND DERIVATIVES THEREOF

[75] Inventors: Theodor Denzel, Regensburg; Hans Hoehn, Tegernheim, both of Germany

[73] Assignee: E. R. Squibb & Sons, Inc., Princeton, N.J.

[22] Filed: Oct. 7, 1975

[21] Appl. No.: 620,467

[52] U.S. Cl. .......................... 424/251; 260/256.4 F
[51] Int. Cl.² ............. A61K 31/505; C07D 401/14
[58] Field of Search ............. 424/251; 260/256.4 F

[56] References Cited
UNITED STATES PATENTS 3,780,047  12/1973  Denzel et al. .................. 260/296 P
3,894,021  7/1975  Denzel et al. .................. 260/256.4 F

*Primary Examiner* — Donald B. Moyer
*Attorney, Agent, or Firm* — Lawrence S. Levinson; Merle J. Smith

[57] ABSTRACT

New 3,11-dihydro-6H-pyrazolo[1,5-a]pyrazolo[4',-3':5,6]-pyrido[4,3-d]pyrimidin-6-one and new derivatives thereof have the general formula

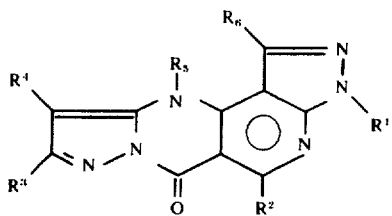

The compounds are useful as anti-inflammatory agents.

22 Claims, No Drawings

3,11-DIHYDRO-6H-PYRAZOLO[1,5-a]PYRAZOLO[4',3':5,6]PYRIDO[4,3-b]PYRIMIDIN-6-ONE AND DERIVATIVES THEREOF

SUMMARY OF THE INVENTION

This invention relates to the new compounds 3,11-dihydro-6H-pyrazolo[1,5-a]pyrazolo[4',3':5,6]pyrido[4,3-d]pyrimidin-6-one, new derivatives and salts thereof. These new compounds have the general formula (I)

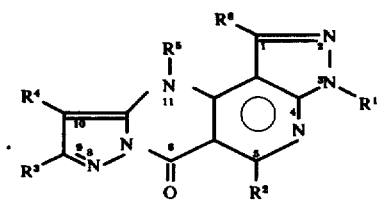

$R^1$ is hydrogen, lower alkyl, phenyl or phenyl-lower alkylene.

$R^2$ is hydrogen or lower alkyl $R^3$ is hydrogen, lower alkyl, phenyl or phenyl-lower alkylene.

$R^4$ is hydrogen or lower alkyl.

$R^5$ is hydrogen, lower alkyl, phenyl-lower alkylene, benzoyl or substituted benzoyl, lower alkanoyl, lower alkoxy-lower alkylene, lower alkylthio-lower alkylene, amino-lower alkylene or di-lower alkylamino-lower alkylene. The basic amino group may also form one of the heterocycles piperidine, morpholine, thiamorpholine or piperazine.

$R_6$ is hydrogen or lower alkyl.

DETAILED DESCRIPTION OF THE INVENTION

The various groups represented by the symbols are of the following types:

The lower alkyl groups are straight or branched chain hydrocarbon groups having up to seven carbon atoms like methyl, ethyl, propyl, isopropyl, butyl, isobutyl, t-butyl, pentyl and the like. The lower alkylene groups are divalent radicals of the same kind. Examples of the phenyl-lower alkylene groups are benzyl, phenethyl, phenylisopropyl and the like. The $C_1$-$C_4$ and especially the $C_1$-$C_2$ lower alkyl and lower alkylene groups are preferred.

The substituted benzoyl groups are simply substituted groups having halogen (the four common halogens, but preferably chlorine or bromine), lower alkyl or lower alkoxy (similar to the lower alkyl groups defined above) groups on the phenyl ring, for example, p-chlorobenzoyl, o-chlorobenzoyl, p-bromobenzoyl, m-bromobenzoyl, p-methylbenzoyl, o-ethylbenzoyl, p-methoxybenzoyl and the like.

The lower alkanoyl groups are the acyl groups of the lower ($C_2$-$C_7$) fatty acids, e.g., acetyl, propionyl, butyryl, isobutyryl and the like. Those with up to four carbons in the chain are preferred, especially acetyl.

The lower alkoxy-lower alkylene and lower alkylthio-lower alkylene groups represented by $R^5$ have radicals like those described above including such groups as methoxy-methylene, ethoxymethylene, methoxyethylene, methylthiomethylene, methylthioethylene, ethylthiomethylene, ethylthioethylene, etc.

The amino-lower alkylene groups are of the same type, e.g., aminomethyl, aminoethyl, etc. The di-lower alkylamino-lower alkylene groups are also of the same type wherein the nitrogen is substituted with two lower alkyl groups. In addition, the two lower alkyl groups may join in forming a heterocycle which may include an additional hetero atom. In other words, the di-lower alkylamino-lower alkylene group can take the form

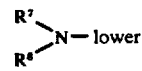

alkylene wherein $R^7$ and $R^8$ are lower alkyl groups or join together to complete the heterocycle piperidine, morpholine, thiamorpholine or piperazine. Preferably the lower alkyl and lower alkylene groups have up to 4 and especially 1 or 2 carbons. Thus, groups like dimethylaminomethyl, diethylaminomethyl, dimethylaminoethyl, diethylaminoethyl, dimethylaminopropyl, piperidinomethyl, piperidinoethyl, morpholinomethyl, morpholinoethyl, thiamorpholinomethyl, thiamorpholinoethyl, piperazinomethyl, piperazinoethyl, piperazinopropyl are included.

Preferably $R^1$ is lower alkyl, especially ethyl; $R^2$ is hydrogen or lower alkyl, especially hydrogen; $R^3$ is hydrogen or lower alkyl, especially hydrogen and methyl; $R^4$ is hydrogen or lower alkyl, especially hydrogen; $R^5$ is lower alkyl, especially methyl, ethyl and isopentyl, or di-lower alkylamino-lower alkylene, especially dimethylaminopropyl and dimethylaminoethyl; $R^6$ is lower alkyl or hydrogen, especially hydrogen.

The products of the examples are representative of the various compounds of this invention and constitute especially preferred embodiments.

The new compounds of formula I are formed by the following series of reactions. The symbols in the structural formulas have the same meaning as previously described.

A pyrazolo [3,4-b]pyridine of the formula (II)

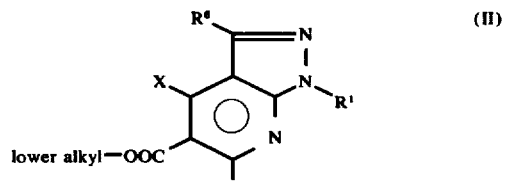

wherein X is halogen, especially chlorine (produced according to the procedure given in U.S. Pat. Nos. 3,773,777, Nov. 20, 1973 and 3,755,340, Aug. 28, 1973) is made to react with an aminopyrazole of the formula (III)

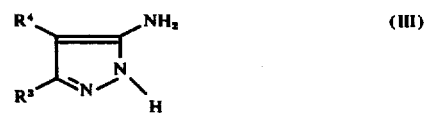

in the presence of a base like triethylamine in an organic solvent such as dimethylformamide at about 100°-120° C. By this reaction a compound of the formula (Ia)

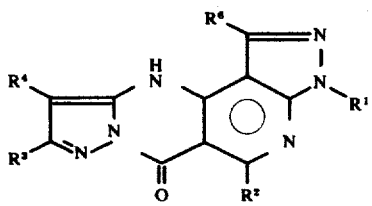

wherein R⁵ is hydrogen is formed.

Compounds of formula I, wherein R⁵ is other than hydrogen and have the meaning as described above, are now formed from compounds of formula Ia by treatment with the appropriate halide R⁵-hal, wherein hal is halogen, preferably chlorine or bromine, in the presence of a strong base like sodium hydride, sodium alcoholate or metallic sodium in a solvent like dimethylformamide or diethylglycol dimethyl ether.

The new compounds of formula I form salts which are also part of this invention. The salts include acid addition salts, particularly the non-toxic, physiologically acceptable members. These salts are formed by reaction with one or more equivalents of a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, aryl- and alkanesulfonates like benzenesulfonate, methanesulfonate, cyclohexanesulfamate and toluenesulfonate, etc. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent or more of acid containing the desired anion.

Additional experimental details are found in the examples.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats.

The compounds of the invention are utilized by formulating in compositions such as tablets, capsules or elixirs for oral administration or in sterile solutions or suspensions for parenteral administration. About 5 to 300 mg. of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

For topical administration as an anti-inflammatory agent, a conventional lotion, ointment or cream containing about 0.01 to 3 percent by weight of a compound of formula I or its salt is formulated.

The following examples are illustrative of the invention and constitute especially preferred embodiments. They also serve as models for the preparation of other members of the group which can be produced by suitable substitution of starting materials. All temperatures are in degrees celsius.

EXAMPLE 1

3-Ethyl-3,11-dihydro-6H-pyrazolo[1,5-a]pyrazolo[4',-3':5,6]-pyrido[4,3-d]pyrimidin-6-one 126 g. of 4-chloro-1-ethyl-1H-pyrazolo[3,4-b]pyridine-5-carboxylic acid ethyl ester (0.5 mol.), 41.5 g. of 5-amino-pyrazole (0.5 mol.) and 50.6 g. of triethylamine (0.5 mol.) are heated at reflux temperature with stirring in 250 ml. of dimethylformamide for 16 hours. After cooling, about 300 ml. of water are added and the white precipitated product, 3-ethyl-3,11-dihydro-6H-pyrazolo[1,5-a]pyrazolo-[4',3':5,6]pyrido[4,3-d]pyrimidin-6-one is filtered off, yield 57.7 g. (45.4%); m.p. >300° (DMF).

EXAMPLE 2

3-Ethyl-3,11-dihydro-11-(3-methylbutyl)-6H-pyrazolo[1,5-a]-pyrazolo[4',3':5,6]pyrido[4,3-d]pyrimidin-6-one 7.6 g. of 3-ethyl-3,11-dihydro-6H-pyrazolo[1,5-a]-pyrazolo[4',3':5,6]pyrido[4,3-d]pyrimidin-6-one (0.03 mol.) are refluxed with stirring in 100 ml. of diethyleneglycol dimethylether together with 1.4 g. of sodium (0.06 mol.). After this time, 11.5 g. of 1-bromo-3-methylbutane (0.075 mol) are added and the mixture is refluxed for 16 hours. The solvent is distilled off and the residue is crystallized with methanol, filtered and washed with water to obtain 3-ethyl-3,11-dihydro-11-(3-methylbutyl)-6H-pyrazolo[1,5-a]-pyrazolo[4',3':5,6]pyrido[4,3-d]pyrimidin-6-one, yield 4.1 g. (42%); m.p. 167°–168° (isopropanol).

EXAMPLE 3

3,11-Diethyl-3,11-dihydro-6H-pyrazolo[1,5-a]pyrazolo[4',3':5,6]-pyrido[4,3-d]pyrimidin-6-one By substituting 0.075 mol. of ethyl bromide for the 1-bromo-3-methylbutane in the procedure of Example 2, 3,11-diethyl-3,11-dihydro-6H-pyrazolo[1,5- a]pyrazolo[4', 3':5,6]pyrido[4,3-d]pyrimidin-6-one is obtained, yield 58%, m.p. 277°–279° (DMF).

EXAMPLE 4

3-Ethyl-3,11-dihydro-11-methyl-6H-pyrazolo[1,5-a]pyrazola-[4',3':5,6]pyrido[4,3-d]pyrimidin-6-one By substituting 0.075 mol. of methyl bromide for the 1-bromo-3-methylbutane in the procedure of Example 2, 3-ethyl-3,11-dihydro-11-methyl-6H-pyrazolo[1,5-a]pyrazolo-[4',3':5,6]pyrido[4,3-d]pyrimidin-6-one is obtained; yield 61%, m.p. 276°–278° (DMF).

EXAMPLE 5

3-Ethyl-3,11-dihydro-11-[(dimethylamino)propyl]-6H-pyrazolo-[1,5-a]pyrazolo[4',3':5,6]pyrido[4,3-d]pyrimidin-6-one By substituting 0.075 mol. of 3-(dimethylamino)propyl chloride for the 1-bromo-3-methylbutane in the procedure of Example 2,3-ethyl-3,11-dihydro-11-[(dimethylamino)-propyl( ]-6H-pyrazolo[1,5-a]pyrazolo[4',3':5,6]pyrido[4,3; -d]-pyrimidin-6-one is obtained; yield 56%, m.p. 165°–168° (isopropanol). Treatment of the product with ethanolic HCl yields the hydrochloride salt.

EXAMPLE 6

3-Ethyl-3,11-dihydro-9-methyl-6H-pyrazolo[1,5-a]pyrazolo-[4',3':5,6]pyrido[4,3-d]pyrimidin-6-one By replacing the 5-aminopyrazole with 5-amino-3-methylpyrazole in the procedure of Example 1, 3-ethyl-3,11-dihydro-9-methyl-6H-pyrazolo[1,5-a]pyrazolo[-4',3':5,6]-pyrido[4,3-d]pyrimidin-6-one is obtained, yield 63.2%, m.p. >300° (DMF).

EXAMPLE 7

3-Ethyl-3,11-dihydro-9,11-dimethyl-6H-pyrazolo[1,5-a]-pyrazolo[4', 3':5,6]pyrido[4,3-d]pyrimidin-6-one 8.05 g. of 3-ethyl-3,11-dihydro-9-methyl-6H-pyrazolo[1,5-a]pyrazolo[4.40 ,3':5,6]pyrido[4,3-d]pyrimidin-6-one (0.03 mol.) are refluxed with stirring in 100 ml. of diethyleneglycol dimethylether together with 0.9 g. of sodium (0.04 mol.) for 2 hours. After this time, 14.2 g. of methyl iodide (0.1 mol.) are added and heating is continued for 12 hours. The solvent is removed in vacuo and the residue crystallized with methanol, filtered and washed with water to obtain 3-ethyl-3,11-dihydro-9,11-dimethyl-6H-pyrazolo[1,5-a]pyrazolo[4', 3':5,6]pyrido[4,3-d]-pyrimidin-6-one, yield 5.2 g. (61%), m.p. 306°–307° (methanol).

EXAMPLE 8

3,11-Diethyl-3,11-dihydro-9-methyl-6H-pyrazolo[1,5-a]-pyrazolo[4',3+:5,6]pyrido[4,3-d]pyrimidin-6-one By substituting 0.1 mol. of ethyl iodide for the methyl iodide in the procedure of Example 7, 3,11-diethyl-3,11-dihydro-9-methyl-6H-pyrazolo[1,5-a]pyrazolo[-4',3':5,6]-pyrido[4,3-d]pyrimidin-6-one is obtained, yield 54%, m.p. 255°–256° (methanol).

EXAMPLE 9

3-Ethyl-3,11-dihydro-9-methyl-11-(3-methylbutyl)-6H-pyrazolo[1,5-a]pyrazolo[4',3':5,6]pyrido[4,3-d]pyrimidin-6-one By substituting 0.1 mol. of 1-bromo-3-methylbutane for the methyl iodide in the procedure of Example 7, 3-ethyl-3,11-dihydro-9-methyl-11-(3-methylbutyl)-6H-pyrazolo[1,5-a]pyrazolo[4',3':5,6]pyrido[4,3-d]pyrimidin-6-one is obtained, yield 48%, m.p. 271°–272° (butanol).

EXAMPLE 10

3-Ethyl-3,11-dihydro-9-methyl-11-[(3-dimethylamino)propyl]-6H-pyrazolo[1,5-a]pyrazolo[4',-3':5,6]pyrido[4,3-d]pyrimidin-6-one By substituting 0.1 mol. of (3-dimethylamino)propyl bromide for the methyl iodide in the procedure of Example 7, 3-ethyl-3,11-dihydro-9-methyl-11-[(3-dimethylamino)propyl]-6H-pyrazolo[1,5-a]pyrazolo[4',-3':5,6]pyrido[4,3-d]pyrimidin-6-one is obtained. Treatment of the product with acetic acid yields the acetate salt.

EXAMPLE 11

3-Ethyl-3,11-dihydro-9-methyl-11-[(2-dimethylamino)ethyl]-6H-pyrazolo[1,5-a]pyrazolo[4',-3':5,6|pyrido|4,3-d]pyrimidin-6-one By substituting 0.1 mol. of (2-dimethylamino)ethyl chloride for the methyl iodide in the procedure of Example 7, 3-ethyl-3,11-dihydro-9-methyl-11-[(2-dimethylamino)ethyl]-6H-pyrazolo[1,5-a]pyrazolo[-4',3+:5,6]pyrido[4,3-d]pyrimidin-6-one is obtained.

EXAMPLE 12

3-Ethyl-3,11-dihydro-1,5-dimethyl-6H-pyrazolo[1,5-a]pyrazolo-[4',3':5,6]pyrido[4,3:d]pyrimidin-6-one By substituting 0.5 mol. of 4-chloro-3,6-dimethyl-1-ethyl-1H-pyrazolo[3,4-b]pyridine-5-carboxylic acid ethyl ester for the 4-chloro-1-ethyl-1H-pyrazolo[4,3-b]pyridine-5-carboxylic acid ethyl ester in the procedure of Example 1, 3-ethyl-3,11-dihydro-1,5-dimethyl-6H-pyrazolo[1,5-a]pyrazolo-[4',3':5,6]pyrido[4,3-d]pyrimidin-6-one is obtained.

EXAMPLE 13

3,11-Diethyl-3,11-dihydro-1,5-dimethyl-6H-pyrazolo[1,5a]-pyrazolo[4',3':5,6]pyrido[4,3-d]pyrimidin-6-one By treating the product of Example 12 with 0.1 mol. of ethyl iodide according to the procedure of Example 7, 3,11-diethyl-3,11-dihydro-1,5-dimethyl-6H-pyrazolo[1,5-a]-pyrazolo[4',3':5,6]pyrido[4,3-d]pyrimidin-6-one is obtained.

EXAMPLE 14

3,10-Diethyl-3,11-dihydro-6H-pyrazolo[1,5-a]pyrazolo[4',3':5,6]-pyrido[4,3-d]pyrimidin-6-one By substituting 0.5 mol. of 5-amino-4-ethylpyrazole for the 5-aminopyrazole in the procedure of Example 1,3,10-diethyl-3,11-dihydro-6H-pyrazolo[1,5-a]pyrazolo[4', 3':5,6]-pyrido[4,3-d]pyrimidin-6-one is obtained.

EXAMPLE 15

3,10-Diethyl-3,11-dihydro-11-piperidinomethyl-6H-pyrazolo-[1,5-a]pyrazolo[4',3':5,6]pyrido[4,3-d]pyrimidin-6-one By treating the product of Example 14 according to the procedure of Example 2 but substituting 0.1 mol. of piperidinomethyl chloride for the 1-bromo-3-methylbutane, 3,10-diethyl-3,11-dihydro-11-piperidinomethyl-6H-pyrazolo-[1,5-a]pyrazolo[4',3':5,6]pyrido[4,3-d]pyrimidin-6-one is obtained.

EXAMPLE 16

3-Ethyl-3,11-dihydro-11-(1-piperazino)methyl-6H-pyrazolo-[1,5-a]pyrazolo[4',3':5,6]pyrido[4,3-d]pyrimidin-6-one By reacting the product of Example 1 with piperazinomethyl chloride instead of 1-bromo-3-methylbutane as in Example 2, 3-ethyl-3,11-dihydro-11-(1-piperazino)methyl-6H-pyrazolo[1,5-a]pyrazolo[4', 3':5,6]pyrido[4,3-d]pyrimidin-6-one is obtained.

EXAMPLE 17

3-Ethyl-3,11-dihydro-9-methyl-11-(2-morpholinoethyl)-6H-pyrazolo[1,5-a]pyrazolo[4',3':5,6-]pyrido[4,3-d]pyrimidin-6-one By reacting the product of Example 6 with 2-morpholinoethyl chloride instead of methyl iodide as in Example 7, 3-ethyl-3,11-dihydro-9-methyl-11-(2-morpholinoethyl)-6H-pyrazolo[1,5-a]pyrazolo[4',3':5,6-]pyrido[4,3-d]pyrimidin-6-one is obtained.

EXAMPLE 18

3-Ethyl-3,11-dihydro-9-methyl-11-thiamorpholinomethyl-6H-pyrazolo[1,5-a]pyrazolo[4',3':5,6-]pyrido[4,3-d]pyrimidin-6-one By reacting the product of Example 6 with thiamorpholinomethyl chloride instead of methyl iodide as in Example 7, 3-ethyl-3,11-dihydro-9-methyl-11-thiamorpholinomethyl-6H-pyrazolo[1,5-a]pyrazolo[4',3':5,6-]pyrido[4,3-d]pyrimidin-6-one is obtained.

EXAMPLE 19

3,11-Dihydro-9-ethyl-6H-pyrazolo[1,5-a]pyrazolo[4',-3':5,6]-pyrido[4,3-d]pyrimidin-6-one By replacing the 5-aminopyrazole with 5-amino-3-ethylpyrazole and the 4-chloro-1-ethyl-1H-pyrazolo[3,4-b]-pyridine-5-carboxylic acid ethyl ester with 4-chloro-1H-pyrazolo[3,4-b]pyridine-5-carboxylic acid ethyl ester in the procedure of Example 1, 3,11-dihydro-9-ethyl-6H-pyrazolo[1,5-a]pyrazolo[4',-3':5,6]pyrido[4,3-d]pyrimidin-6-one is obtained.

EXAMPLE 20

3,11-Dihydro-9-ethyl-11-phenylmethyl-6H-pyrazolo[1,5-a]-pyrazolo[4',3':5,6]pyrido[4,3-d]pyrimidin-6-one By treating the product of Example 19 with 0.1 mol. of benzyl iodide according to the procedure of Example 7, 3,11-dihydro-9-ethyl-11-phenylmethyl-6H-pyrazolo[1,5-a]-pyrazolo[4',3':5,6]pyrido[4,3-d]pyrimidin-6-one is obtained.

EXAMPLE 21

3-Phenylethyl-3,11-dihydro-6H-pyrazolo[1,5-a]pyrazolo-[4',3':5,6-]pyrido[4,3-d]pyrimidin-6-one By replacing the 4-chloro-1-ethyl-1H-pyrazolo[3,4-b]-pyridine-5-carboxylic acid ethyl ester with 1-phenylethyl-4-chloro-1H-pyrazolo[3,4-b]pyridine-5-carboxylic acid ethyl ester in the procedure of Example 1, 3-phenylethyl-3,11-dihydro-6H-pyrazolo[1,5-a]pyrazolo[4', 3':5,6]pyrido[4,3-d]-pyrimidin-6-one is obtained.

EXAMPLE 22

3-Phenylmethyl-3,11-dihydro-11-(2-aminoethyl)-6H-pyrazolo-[1,5-a]pyrazolo[4',3':5,6]pyrido[4,3-d]pyrimidin-6-one By treating the product of Example 21 with aminoethyl bromide instead of 1-bromo-3-methylbutane as in Example 2, 3-phenylmethyl-3,11-dihydro-11-(2-aminoethyl)-6H-pyrazolo-[1,5-a]pyrazolo[4',3':5,6-]pyrido[4,3-d]pyrimidin-6-one is obtained.

EXAMPLE 23

3-Phenyl-3,11-dihydro-6H-pyrazolo[1,5-a]pyrazolo[4', 3':5,6]-pyrido[4,3-d]pyrimidin-6-one By replacing the 4-chloro-1-ethyl-1H-pyrazolo[3,4-b]-pyridine-5-carboxylic acid ethyl ester with 4-chloro-1-phenyl-1H-pyrazolo[3,4-b]pyridine-5-carboxylic acid ester in the procedure of Example 1, 3-phenyl-3,11-dihydro-6H-pyrazolo[1,5-a]pyrazolo[4',3':5,6-]pyrido[4,3-d]pyrimidin-6-one is obtained.

EXAMPLE 24

3-Phenyl-3,11-dihydro-11-methoxyethyl-6H-pyrazolo[1,5-a]-pyrazolo[4',3':5,6]pyrido[4,3-d]pyrimidin-6-one By treating the product of Example 23 with methoxyethyl bromide instead of 1-bromo-3-methylbutane according to the procedure of Example 2,3-phenyl-3,11-dihydro-11-methoxyethyl-6H-pyrazolo[1,5-a]pyrazolo[4',3':5,6]pyrido-[4,3-d]pyrimidin-6-one is obtained.

EXAMPLE 25

3,9-Diethyl-3,11-dihydro-6H-pyrazolo[1,5-a]pyrazolo[4', 3':5,6]-pyrido[4,3-d]pyrimidin-6-one By replacing the 5-aminopyrazole with 5-amino-3-ethylpyrazole in the procedure of Example 1, 3,9-diethyl-3,11-dihydro-6H-pyrazolo[1,5-a]pyrazolo[4',3':5,6-]pyrido-[4,3-d]pyrimidin-6-one is obtained.

EXAMPLE 26

3,9-Diethyl-3,11-dihydro-11-benzoyl-6H-pyrazolo[1,5-a]-pyrazolo[4',3':5,6]pyrido[4,3-d]pyrimidin-6-one By treating the product of Example 25 with benzoyl bromide according to the procedure of Example 2, 3,9-diethyl-3,11dihydro-11-benzoyl-6H-pyrazolo[1,5-a]pyrazolo-[4',3':5,6]pyrido[4,3-d]pyrimidin-6-one is obtained.

EXAMPLE 27

3,9-Diethyl-3,11-dihydro-11-(4-chlorobenzoyl)-6H-pyrazolo-[1,5-a]pyrazolo[4',3':5,6]pyrido[4,3-d]pyrimidin-6-one

By treating the product of Example 25 with 4-chlorobenzoyl chloride according to the procedure of Example 2, 3,9-diethyl-3,11-dihydro-11-(4-chlorobenzoyl)-6H-pyrazolo-[1,5-a]pyrazolo[4', 3':5,6]pyrido[4,3;-d]pyrimidin-6-one is obtained.

EXAMPLE 28

3-Ethyl-3,11-dihydro-11-propionyl-6H-pyrazolo[1,5-a]pyrazolo[4', 3':5,6]pyrido[4,3-d]pyrimidin-6-one

By treating the product of Example 1 with propionyl bromide instead of 1-bromo-3-methylbutane as in Example 2, 3-ethyl-3,11-dihydro-11-propionyl-6H-pyrazolo[1,5-a]pyrazolo-[4',3':5,6]pyrido[4,3-d]pyrimidin-6-one, is obtained.

EXAMPLE 29

3-Ethyl-3,11-dihydro-9-phenyl-6H-pyrazolo[1,5-a]pyrazolo-[4', 3':5,6]pyrido[4,3 -d]pyrimidin-6-one

By replacing the 5-aminopyrazole with 5-amino-3-phenylpyrazole in the procedure of Example 1, 3-ethyl-3,11-dihydro-9-phenyl-6H-pyrazolo[1,5-a]pyrazolo[-4',3':5,6]-pyrido[4,3-d]pyridin-6-one is obtained.

EXAMPLE 30

3-Ethyl-3,11-dihydro-9-phenyl-11-methylthiomethyl-6H-pyrazolo[1,5-a]pyrazolo[4',3':5,6]pyrido[4,3-d]pyrimidin-6-one

By treating the product of Example 29 with methylthiomethyl bromide according to the procedure of Example 2, 3-ethyl-3,11-dihydro-9-phenyl-11-methylthiomethyl-6H-pyrazolo[1,5-a]pyrazolo[4',3':5,6-]pyrido[4,3-d]pyrimidin-6-one is obtained.

EXAMPLE 31

3-Ethyl-3,11-dihydro-9-phenylethyl-6H-pyrazolo[1,5-a]pyrazolo[4',3':5,6]pyrido[4,3-d]pyrimidin-6-one

By replacing the 5-aminopyrazole with 5-amino-3-phenylethylpyrazole in the procedure of Example 1, 3-ethyl-3,11-dihydro-9-phenylethyl-6H-pyrazolo[1,5-a]pyrazolo[4',3':5,6]pyrido[4,3-d]pyrimidin-6-one is obtained.

EXAMPLE 32

3-Ethyl-3,11-dihydro-9-phenylethyl-11-(3-methoxy)-benzoyl-6H-pyrazolo[1,5-a]pyrazolo[4',3':5,6-]pyrido[4,3-d]pyrimidine-6-one

By treating the product of Example 31 with 3-methoxybenzoyl bromide as in Example 2, 3-ethyl-3,11-dihydro-9-phenylethyl-11-(3-methoxy)benzoyl-6H-pyrazolo[1,5-a]-pyrazolo[4',3':5,6]pyrido[4,3-d]pyrimidine-6-one is obtained.

EXAMPLE 33

3,11-Dihydro-6H-pyrazolo[1,5-a]pyrazolo[4',3':5,6-]pyrido[4,3-d]pyrimidine-6-one

By replacing the 4-chloro-1-ethyl-1H-pyrazolo[3,4-b]-pyridine-5-carboxylic acid ethyl ester with 4-chloro-1H-pyrazolo[3,4-b]pyridine-5-carboxylic acid ethyl ester in the procedure of Example 1, 3,11-dihydro-6H-pyrazolo[1,5-a]-pyrazolo[4',3':5,6]pyrido[4,3-d]pyrimidine-6-one is obtained.

EXAMPLE 34

The following ingredients are used to make 1,000 200 mg. tablets each containing 100 mg. of active ingredient:

3-Ethyl-3,11-dihydro-9-methyl-6H-pyrazolo[1,5-a]pyrazola[4',3':5,6]-pyrido[4,3-d]pyrimidine-6-one: 100 gm.
Polyvinyl pyrrolidone: 7.5 gm.
Lactose: 20 gm.
Magnesium stearate: 3.5 gm.
Corn starch: 17.5 gm.
Avicel (microcrystalline cellulose): 51.5 gm.

The medicament and lactose are thoroughly admixed. the polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg. tablets on a standard concave punch. The tablets are then veneer coated with methyl cellulose in a spray pan.

What is claimed is:

1. A compound of the formula

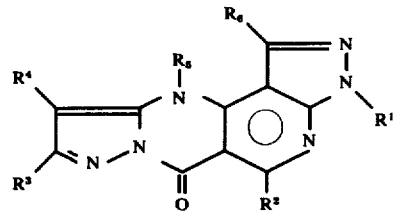

wherein $R^1 R^3$ each is hydrogen, lower alkyl, phenyl or phenyl-lower alkylene;

$R^2$, $R^4$ and $R^6$ each is hydrogen or lower alkyl; $R^5$ is hydrogen, lower alkyl, phenyl-lower alkylene, benzoyl, substituted benzoyl wherein the phenyl substituent is halogen, lower alkyl or lower alkoxy, lower alkanoyl, lower alkoxy-lower alkylene, lower alkylthio-lower alkylene, amino-lower alkylene or

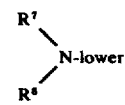

alkylene wherein $R^7$ and $R^8$ each is lower alkyl said lower alkyl, lower alkoxy, lower alkanoyl and lower alkylene each having up to 7 carbon atoms; and acid addition salts thereof.

2. A compound as in claim 1 wherein $R^1$ is lower alkyl; $R^2$, $R^3$, $R^4$ and $R^6$ each is hydrogen or lower alkyl; $R^5$ is lower alkyl or di-lower alkylamino-lower alkylene; and physiologically acceptable acid addition salts thereof.

3. A compound as in claim 1 wherein $R^2$, $R^3$, $R^4$ and $R^6$ each is hydrogen.

4. A compound as in claim 1 wherein $R^1$ is lower alkyl.

5. A compound as in claim 1 wherein $R^3$ is lower alkyl.

6. A compound as in claim 1 wherein $R^3$ is hydrogen.

7. A compound as in claim 1 wherein $R^5$ is hydrogen.

8. A compound as in claim 1 wherein $R^5$ is lower alkyl.

9. A compound as in claim 1 wherein $R^5$ is di-lower alkylamino-lower alkylene.

10. A compound as in claim 1 wherein $R^1$ and $R^3$ each is lower alkyl, $R^2$, $R^4$, $R^5$ and $R^6$ each is hydrogen.

11. A compound as in claim 10 wherein $R^1$ is ethyl and $R^3$ is methyl.

12. A compound as in claim 1 wherein $R^1$ and $R^5$ each is lower alkyl and $R^2$, $R^3$, $R^4$ and $R^6$ each is hydrogen.

13. A compound as in claim 12 wherein $R^1$ is ethyl and $R^5$ is isopentyl.

14. A compound as in claim 12 wherein $R^1$ and $R^5$ each is ethyl.

15. A compound as in claim 1 wherein $R^1$, $R^3$ and $R^5$ each is lower alkyl and $R^2$, $R^4$ and $R^6$ each is hydrogen.

16. A compound as in claim 1 wherein $R^1$ and $R^3$ each is lower alkyl, $R^2$, $R^4$ and $R^6$ each is hydrogen and $R^5$ is di-lower alkylamino-lower alkylene.

17. A compound as in claim 16 wherein $R^1$ is ethyl, $R^3$ is methyl and $R^5$ is dimethylaminopropyl.

18. A compound as in claim 1 wherein $R^1$ is lower alkyl, $R^2$, $R^3$, $R^4$ and $R^6$ each is hydrogen and $R^5$ is di-lower alkyl-amino-lower alkylene.

19. A compound as in claim 18 wherein $R^1$ is ethyl and $R^5$ is dimethylaminopropyl.

20. An anti-inflammatory composition comprising an effective amount of a compound of claim 1 and a physiologically acceptable carrier therefor.

21. An anti-inflammatory composition comprising an effective amount of a compound of claim 11 and a physiologically acceptable carrier therefor.

22. A method for treating inflammatory conditions which comprises administering to a mammal suffering therefrom a composition comprising about 5 to 300 mg. of a compound of claim 1 and a physiologically acceptable carrier therefor.

* * * * *